United States Patent

Nakamura et al.

[19]

[11] Patent Number: 6,030,347

[45] Date of Patent: Feb. 29, 2000

[54] BIOLOGICAL-SIGNAL DETECTING DEVICE

[75] Inventors: Katsuji Nakamura, Higashiazai-gun; Hiroyuki Noda, Hikone; Yoshinori Matsue, Hikone; Satoru Makita, Hikone; Kazumi Ookawa, Hikone; Haruo Sugai, Hikone, all of Japan

[73] Assignee: Matsushita Electric Works, Ltd., Osaka, Japan

[21] Appl. No.: 08/875,761

[22] PCT Filed: Jan. 9, 1997

[86] PCT No.: PCT/JP97/00027

§ 371 Date: Aug. 8, 1997

§ 102(e) Date: Aug. 8, 1997

[87] PCT Pub. No.: WO97/24976

PCT Pub. Date: Jul. 17, 1997

[30] Foreign Application Priority Data

Jan. 12, 1996 [JP] Japan ............................... P08-004309
Mar. 15, 1996 [JP] Japan ............................... P08-059592

[51] Int. Cl.[7] .................................................. A61B 5/00
[52] U.S. Cl. ................................ 600/552; 600/595
[58] Field of Search ................................... 600/587, 592, 600/595, 552, 534

[56] References Cited

U.S. PATENT DOCUMENTS

| 4,981,307 | 1/1991 | Walsh ............................... 280/290 |
| 5,515,865 | 5/1996 | Scanlon ............................ 600/534 |
| 5,620,003 | 4/1997 | Sepponen ......................... 600/595 |

FOREIGN PATENT DOCUMENTS

| 54-42884 | 4/1979 | Japan. |
| 60-49200 | 3/1985 | Japan. |
| 5-317374 | 12/1993 | Japan. |
| 6-34401 | 2/1994 | Japan. |

*Primary Examiner*—Cary E. O'Connor
*Assistant Examiner*—Pamela P. Wingood
*Attorney, Agent, or Firm*—Nikaido, Marmelstein, Murray & Oram LLP

[57] ABSTRACT

A biological-signal detecting device of a non-wrapper type for accurately detecting a biological signal of a user such as heartbeat number, respiration number or blood pressure, comprises a frame, a spring net fixed to the frame and having an elastic deformation capability to support a weight of the user, and a biological-signal detecting unit. The detecting unit is disposed on a second supporting surface of the spring net opposed to a first supporting surface of the spring net for receiving the weight of the user. The detecting unit determines the biological signal of the user according to a biological vibration which is a cyclic, minute load-variation of the user transmitted through the spring net when the weight of the user is supported by the spring net.

11 Claims, 11 Drawing Sheets

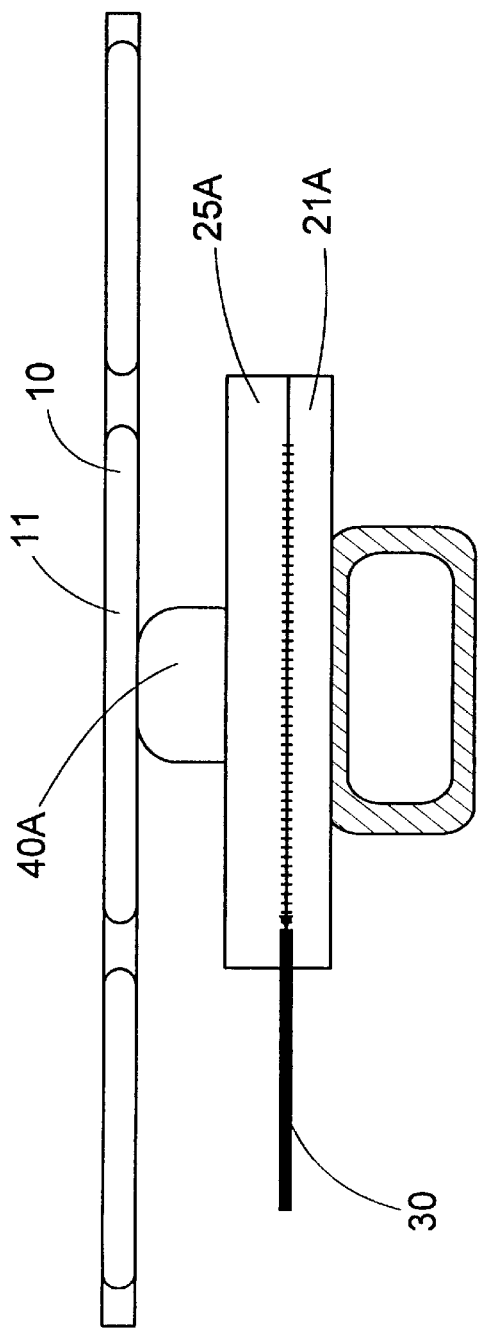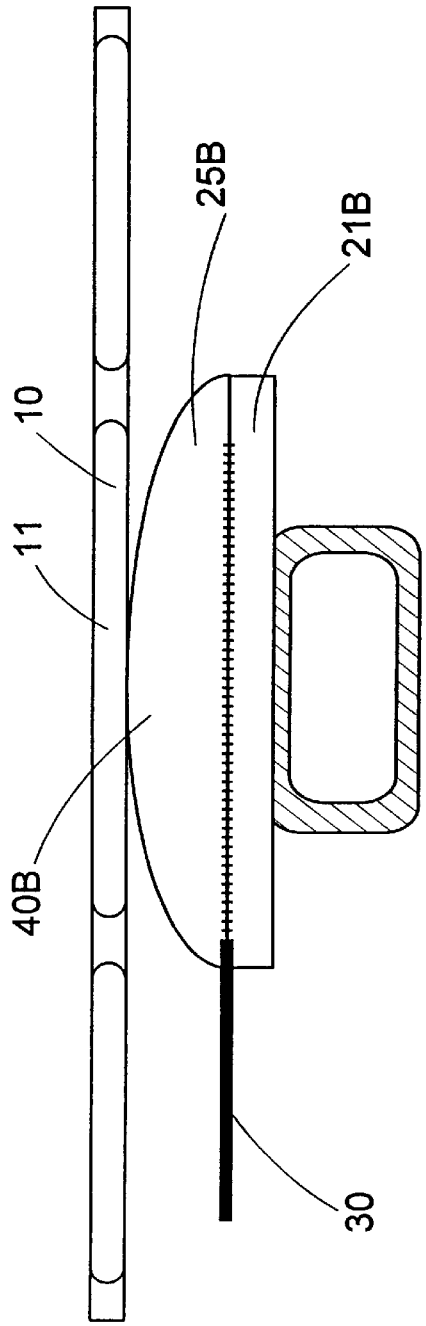

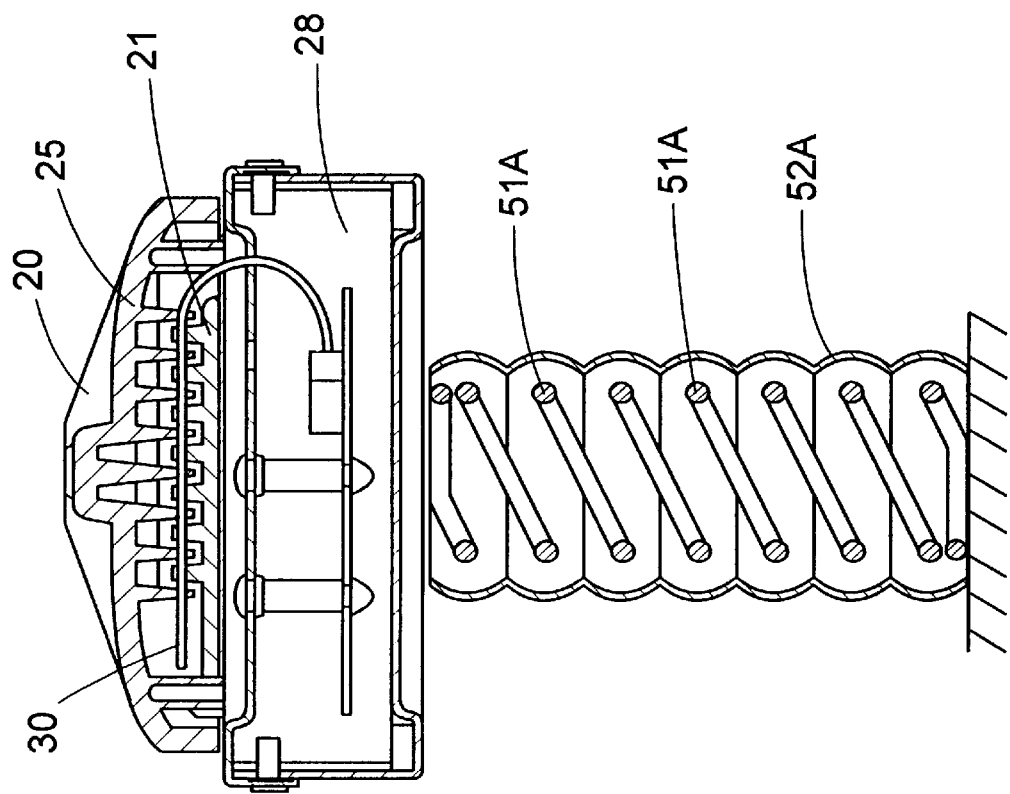
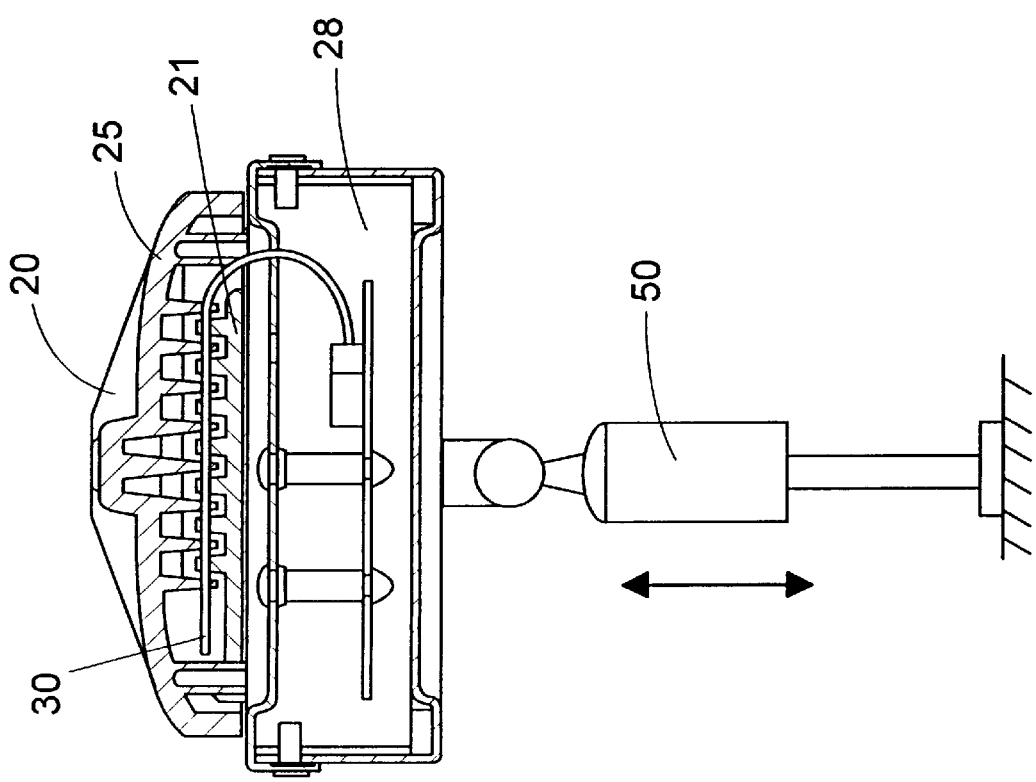
FIG. 12
FIG. 11

BIOLOGICAL-SIGNAL DETECTING DEVICE

BACKGROUND OF THE INVENTION

1. Field of the Invention

The present invention relates to a biological-signal detecting device of a non-wrapper type having a structure for supporting a user such as a chair, bed or a massager, and a biological-signal detector mounted on the structure to accurately detect a biological signal of the user such as heartbeat number, respiration number or blood pressure.

2. Disclosure of the Prior Art

In a biological-signal detecting device of a wrapper type, a sensor for detecting a biological information of a user such as heartbeat number, respiration number or blood pressure, is directly fitted to the user. Since the fitted sensor gives a kind of uncomfortable feeling (stress) to the user, it makes difficult to accurately detect of the biological signal of the user at a relax state. In other words, the fitted sensor will detect the biological signal of the user at a stress state. In particular, there is a possibility that when a sensor is directly stuck on a body surface of the user to detect the biological signal, it brings about an inflammation to the user's skin. From these reasons, a biological-signal detecting device of a non-wrapper type is proposed. In this type, the biological information of the user can be detected without the sensor being directly fitted to the user. In general, this detecting device of the non-wrapper type comprises a structure for supporting the user, such as a chair, bed or a massager, and a biological-signal detector mounted to the structure to detect the biological information of the user.

However, when an arrangement of the detector on the structure is not adequate for the user, the detector will give a feeling of oppression to the user. Consequently, it will be often difficult to induce the user to the relax state. To prevent the occurrence of such a feeling of oppression, the detector would be preferably arranged to the structure so as to be spaced away from the user. In this case, there is a problem of decreasing a detection accuracy of the biological signal. The detection accuracy often changes in accordance with a position of the user on the structure, i.e., a positional relation between the user sitting on a chair and a detector mounted on the chair. In addition, due to a small movement of the user in a bed for detecting the biological information, for example, a rolling-over of the user in the bed, the detection accuracy will change in accordance with a positional relation between the user lying in the bed and a detector attached to the bed.

SUMMARY OF THE INVENTION

For improving the above problems, a primary object of the present invention is to provide a biological-signal detecting device for accurately detecting a biological signal of a user at a relax state without providing an uncomfortable feeling to the user. That is, this detecting device comprises a frame, a spring net fixed to the frame and having an elastic deformation capability for supporting a weight of a user, and a biological-signal detecting unit disposed on the spring net. The spring net has a first supporting surface for receiving the weight of the user and a second supporting surface opposed to the first supporting surface. The detecting unit is disposed on the second supporting surface. When the weight of the user is supported by the spring net, the detecting unit detects the biological signal of the user according to a biological vibration which is a cyclic, minute load-variation transmitted through the spring net. In the present invention, since the detecting unit is disposed on the spring net, the biological vibration of the user can be stably transmitted to the detecting unit through the spring net even when there is a delicate position change of the user on the spring net, for example, a small movement of the user sitting on the spring net, or a rolling over of the user on the spring net. As a result, it is possible to accurately detect the biological signal of the user while preventing variations in detection accuracy. In addition, since the detecting unit is disposed on the second supporting surface opposed to the first supporting surface of the spring net, it is possible to detect the biological signal at a relax state of the user without providing an uncomfortable feeling to the user.

In a preferred embodiment of the present invention, the spring net used in the biological-signal detecting device comprises a plurality of spring units and coupling members for coupling between the spring units. Each of the spring units is formed by bending a spring material in a wave pattern. The wave pattern is provided with a plurality of linear portions and arcuate portions each extending between adjacent linear portions. In case of using this spring net, it is preferred to dispose the detecting unit on one of the linear portions of the spring units in order to further improve the detection accuracy of the biological signal.

Moreover, it is preferred that the biological-signal detecting unit of the present invention comprises a base, a movable member capable of moving relative to the base according to the biological vibration transmitted through the spring net, an optical fiber having input and output ends, a light source disposed at the input end to supply a light into the optical fiber, an optical sensor disposed at the output end to receive an output light from the optical fiber, and a biological-signal analyzing section for analyzing a change of the output light received by the optical sensor, and determining the biological signal. The optical fiber is disposed between the base and the movable member so as to show an elastic deformation according to a position change of the movable member relative to the base. The elastic deformation brings about a change of an optical property of the optical fiber, i.e., a change of internal reflectance of the optical fiber. Since an amount of light received by the optical sensor changes according to the change of internal reflectance of the optical fiber, the analyzing section analyzes the change of the light amount to determine the biological signal of the user.

In case of using the optical fiber, it is preferred that the biological-signal detecting unit is supported by a supporting unit to prevent a breakage of the optical fiber when the weight of the user is rapidly loaded to the detecting unit. That is, the supporting unit comprises a spring member having a shock absorbing capability to prevent that the weight of the user is rapidly loaded to the optical fiber, and a vibration damping member for preventing a vibration of the detecting unit caused in synchronization with the biological vibration.

These and still other objects and advantages will become apparent from the following description of the preferred embodiments of the invention when taken in conjunction with the attached drawings.

BRIEF DESCRIPTION OF THE DRAWINGS

In FIGS. 5A and 5B.

In FIGS. 7A and 7B.

FIG. 9 is a side view illustrating a movable member having a projection on its top surface;

FIG. 10 is a side view illustrating a movable member having an arcuate top surface;

FIG. 11 is a side view of a gas spring unit for supporting the biological signal detecting unit;

FIG. 12 is a cross-sectional view of a supporting unit of the biological signal detecting unit;

PREFERRED EMBODIMENTS OF THE INVENTION

As shown below, the present invention is explained in detail referring to attached drawings.

Figure 1:
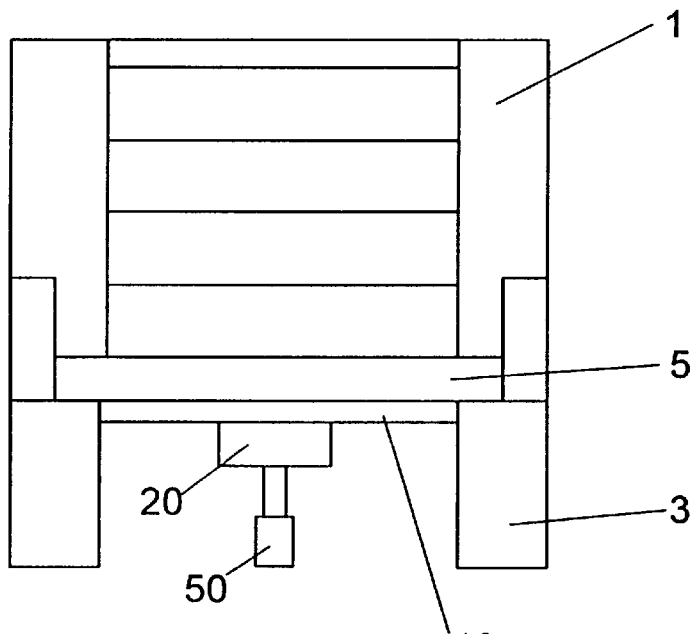
FIG. 1 is a front view of a chair having a biological-signal detecting unit of the present invention.
Figure 2:
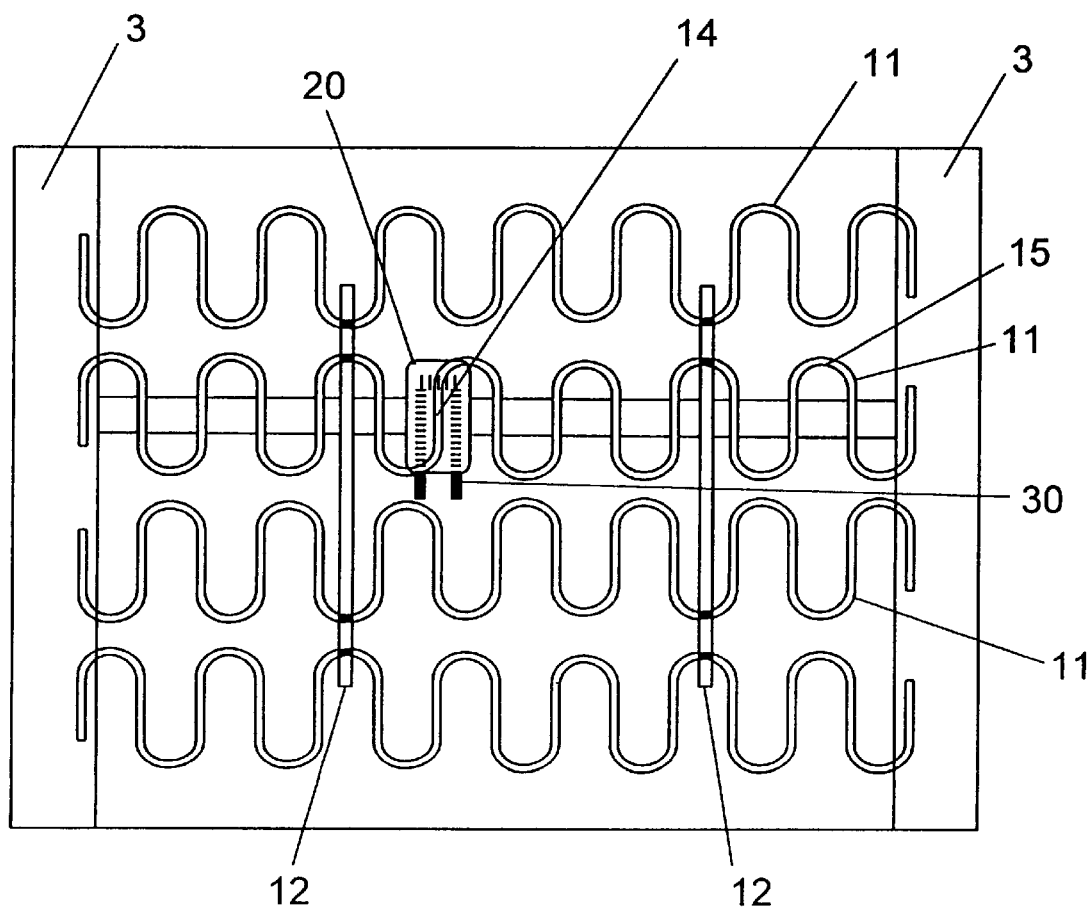
FIG. 2 is a top view of a spring net.

A chair 1 having a biological-signal detecting unit 20 of the present invention is shown in FIG. 1. A spring net 10 for supporting a weight of a user is stretched at a seat portion of the chair. As shown in FIG. 2, this spring net 10 is formed with a plurality of spring units 11 arranged in a row on a same plane, and a pair of coupling members 12 for coupling the spring units. Each of the spring units 11 is fixed to frames 3 of the chair 1 at its opposite ends, and made of a spring material bent in a wave pattern. The wave pattern is composed of linear portions 14 and arcuate portions 15 each extending between adjacent linear portions, as shown in FIG. 2. When a top surface of the spring net for receiving a weight of the user is defined as a first supporting surface, the detecting unit 20 is mounted on a second supporting surface of the spring net opposed to the first supporting surface. When a weight of the user is supported by the spring net 10, the detecting unit 20 detects a biological signal of the user according to a biological vibration which is defined as a cyclic, minute load-variation transmitted through the spring net. In FIG. 1, numeral 5 designates a cushion placed on the first supporting surface.

Figure 3:
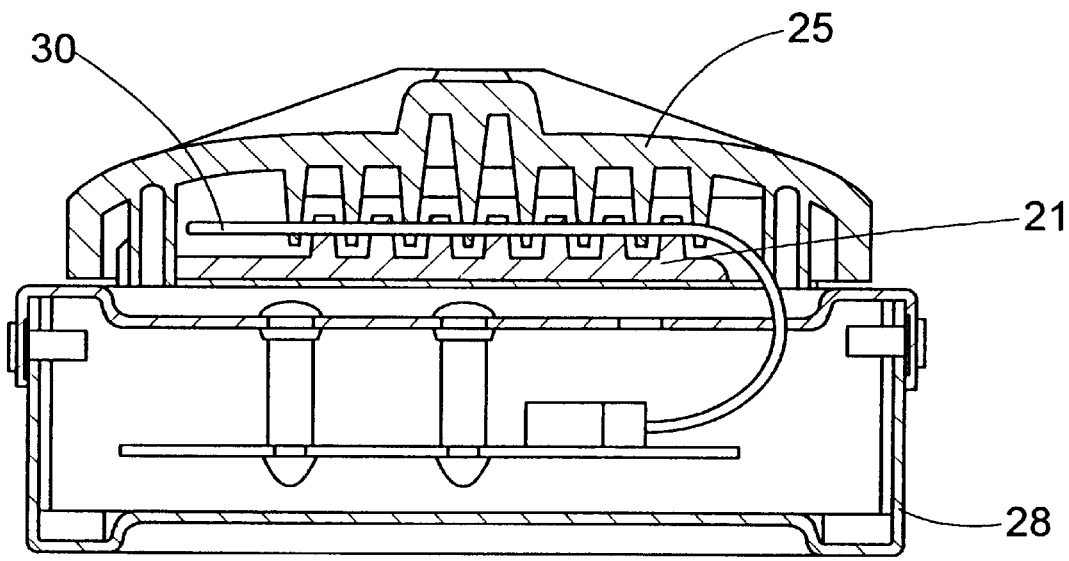
FIG. 3 is a cross-sectional view of the biological-signal detecting unit.
Figure 6:
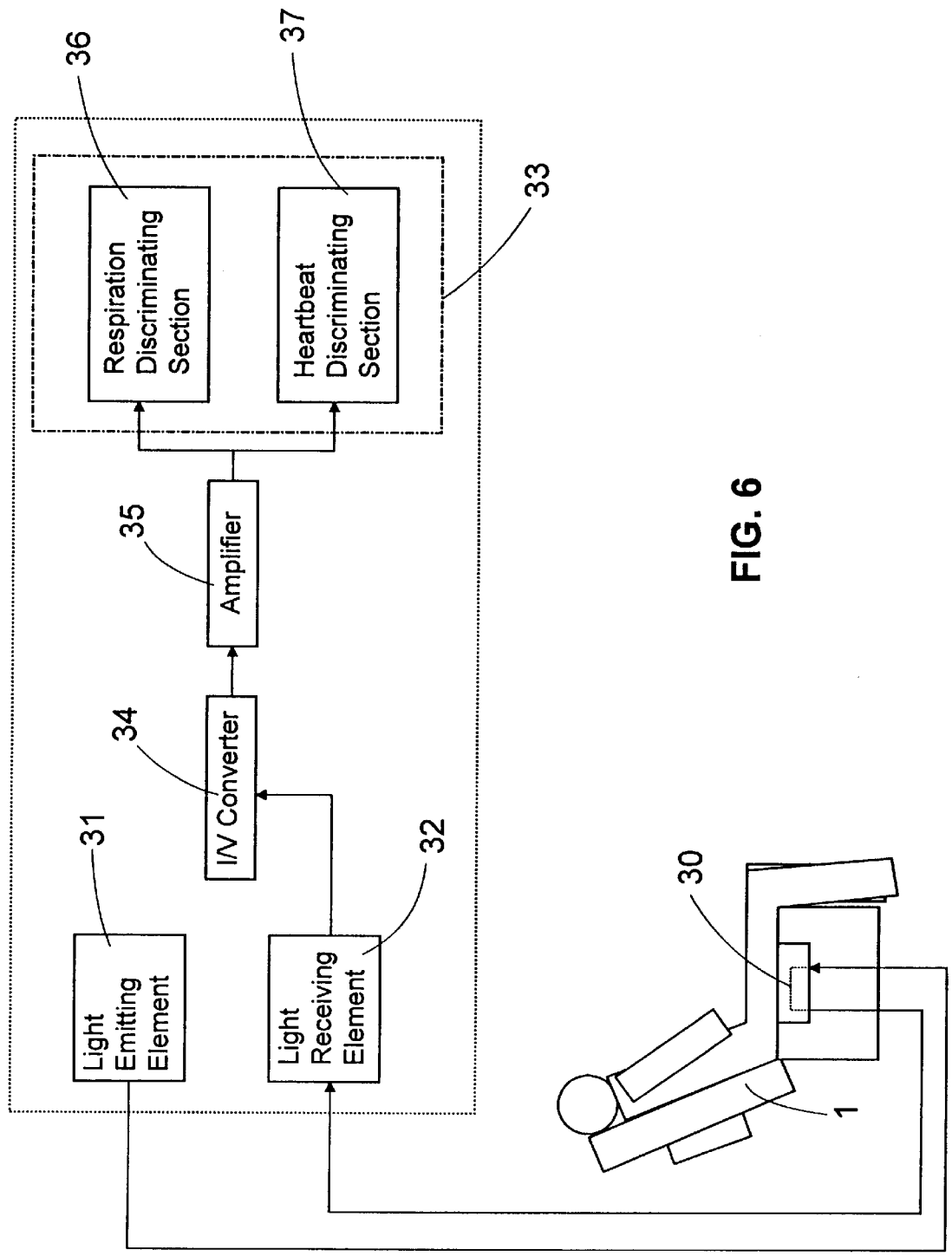
FIG. 6 is a circuit diagram for detecting the biological signal.

As shown in FIGS. 3 and 6, the detecting unit 20 of this embodiment comprises a base 21, a movable member 25 capable of moving relative to the base according to the biological vibration transmitted through the spring net 10, an optical fiber 30 having input and output ends and put between the base and the movable member, a light emitting element 31 such as a light-emitting diode disposed at the input end to supply a light into the optical fiber 30, a light receiving element 32 disposed at the output end to receive a light output from the optical fiber 30, and a biological-signal determining section 33 for analyzing and determining the biological signal according to the light output.

Figure 4:
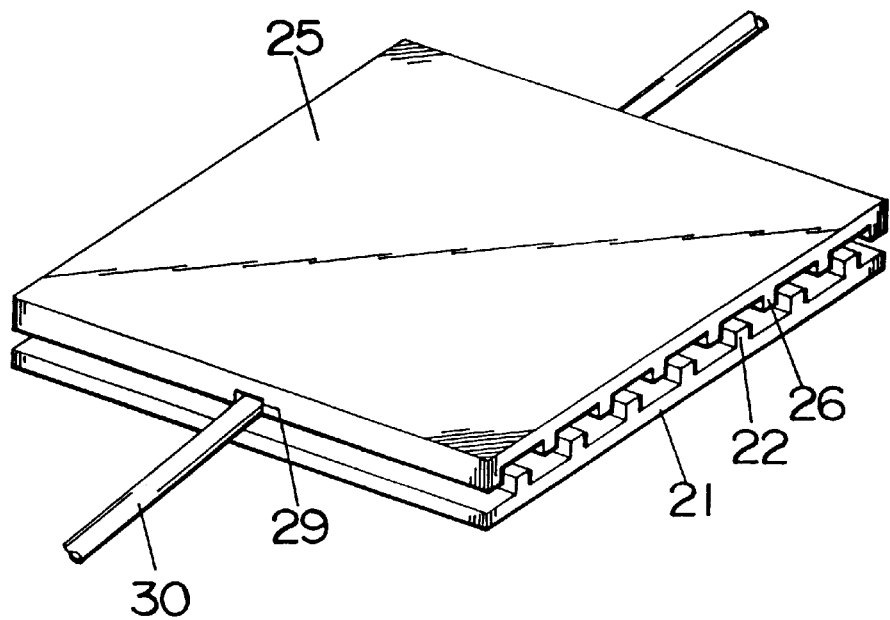
FIG. 4 is a perspective view of an optical fiber arranged between a base and a movable member.
Figure 5A:
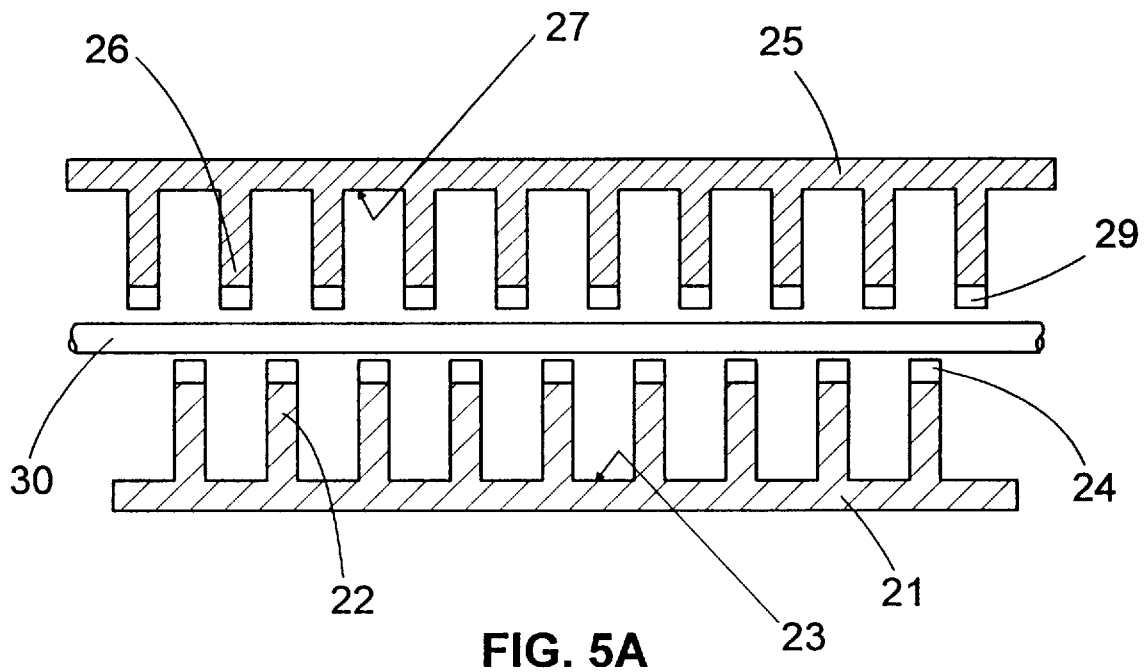
FIG. 5A is a schematic diagram showing the optical fiber between the base and the movable member, in which no load is applied to the movable member.
Figure 5B:
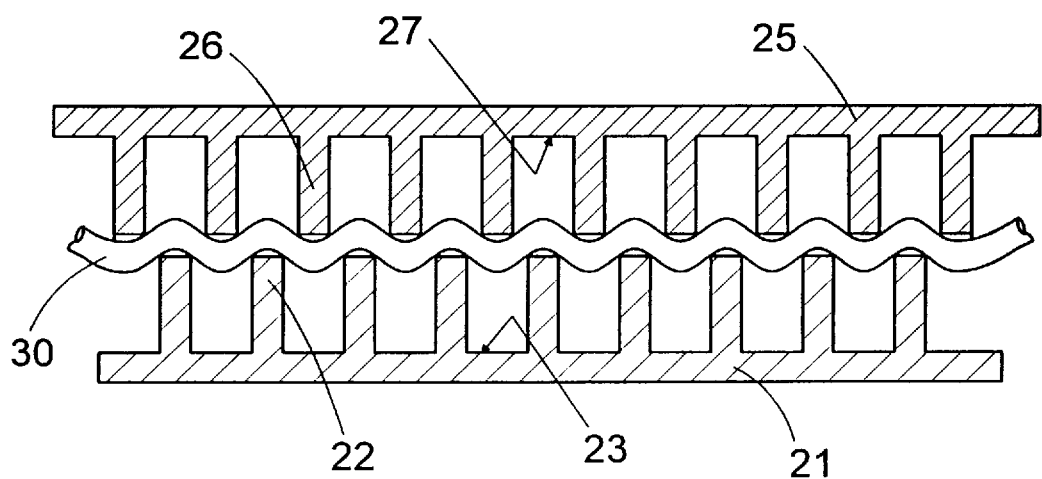
FIG. 5B is a schematic diagram showing the optical fiber put between the base and the movable member, in which a load is applied to the movable member.

In FIG. 4, 5A and 5B, the base 21 and the movable member 25 are briefly drawn to emphasize the optical fiber 30 put between the base 21 and the movable member 25. As shown in these figures, the base 21 has a plurality of first projections 22 arranged at a constant interval, and first grooves 23 each of which is defined between adjacent first projections 22. Similarly, the movable member 25 has a plurality of second projections 26 arranged at a constant interval, and second grooves 27 each of which is defined between adjacent second projections 26. As shown in FIG. 5A, the movable member 25 is disposed upward of the base 21 such that the first projections 22 face to the second grooves 27, and the second projections 26 face to the first grooves 23. When a weight of the user is not loaded to the spring net 10, there is no elastic deformation of the optical fiber 30 between the base 21 and the movable member 25, as shown in FIG. 5A. When a weight of the user is loaded to the spring net 10, the movable member 25 moves toward the base 21, as shown in FIG. 5B, so that an elastic deformation of the optical fiber 30 occurs between the base and the movable member. When a light of the light emitting element 31 is supplied to the optical fiber 30, an amount of light received by the light receiving element 32 changes in accordance with a change of internal reflectance of the optical fiber 30 caused by the elastic deformation of the optical fiber. The biological-signal determining section 33 extracts a delicate change of biological information of the user from the change of light amount to determine the biological signal of the user.

A circuit diagram for detecting the biological signal is shown in FIG. 6. The light receiving element 32 is connected to a respiration discriminating section 36 and a heartbeat discriminating section 37 such as a low-pass filter or a comparator through an I/V converter 34 for converting an current output to a voltage signal and an amplifier 35. In FIG. 3, numeral 28 designates a box fixed to the base 21, in which a detection circuit of the biological signal is incorporated.

The number of elastically-deformed portions of the optical fiber are determined by the numbers of the first and second projections (22, 26). An amount of elastic deformation of the optical fiber, i.e., a curvature of the optical fiber, can be determined by heights of the first and second projections (22, 26). In the drawings, numerals 24 designates a concave formed at a top end of each of the first projection 22. Similarly, numerals 29 designates a concave formed at a top end of each of the second projections 26. These concaves (24, 29) are used to prevent a slip-off of the optical fiber 30 in a horizontal direction from a predetermined position at which the optical fiber should be elastically deformed.

Figure 7A:
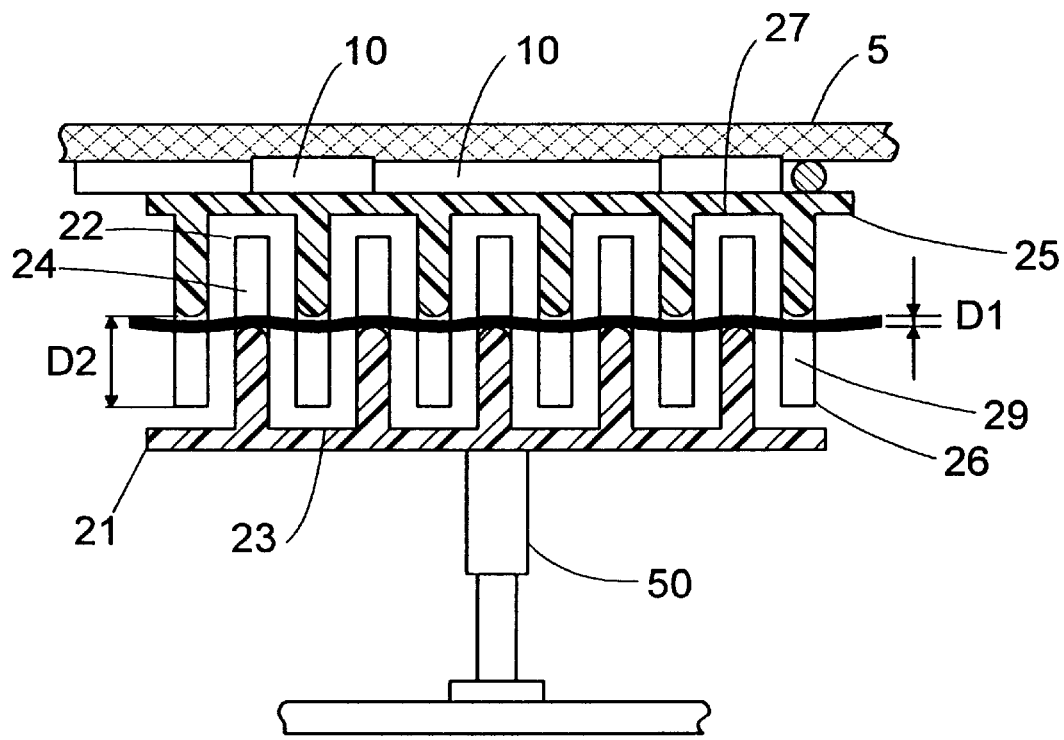
FIG. 7A is a schematic diagram showing an optical fiber between a base and a movable member having a stopper, in which no load is applied to the movable member.
Figure 7B:
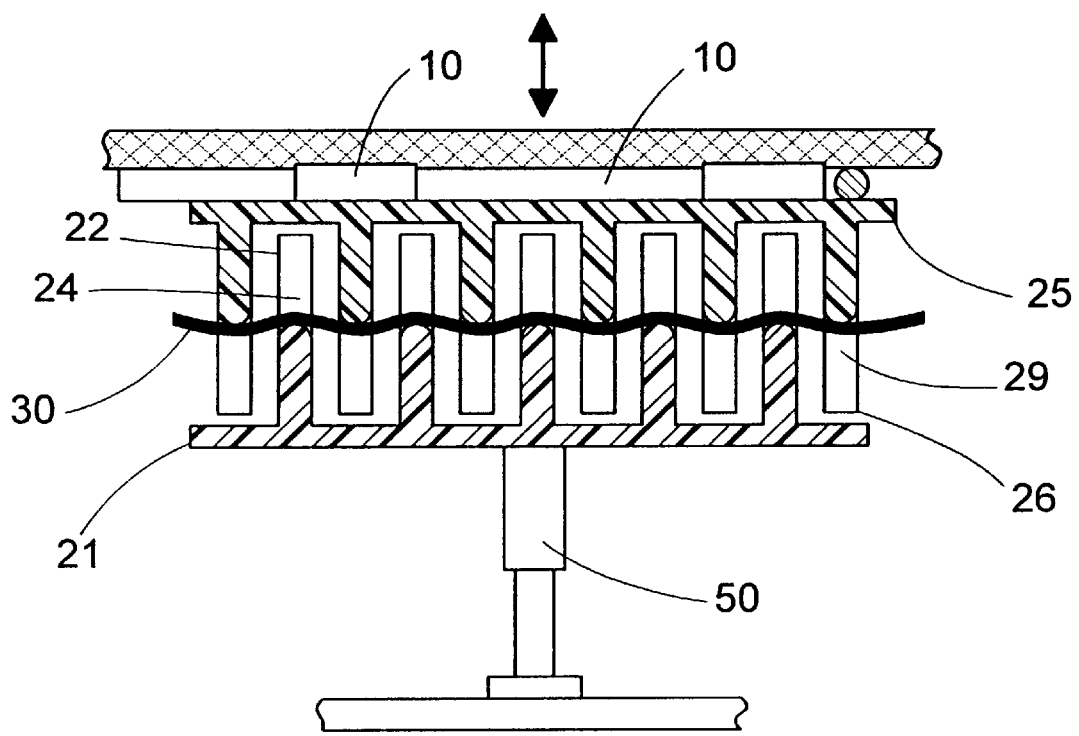
FIG. 7B is a schematic diagram showing the optical fiber put between the base and the movable member, in which a load is applied to the movable member.

By the way, it is preferred that the detecting unit 20 has a stopper for limiting a relative movement of the movable member 25 to the base 21 such that the amount of elastic deformation of the optical fiber 30 is less than a predetermined value. This is useful to prevent a breakage of the optical fiber 30. For example, as shown in FIGS. 7A and 7B, a depth D2 of each of the concaves (24, 29) is larger than a diameter D1 of the optical fiber 30 (D2>D1). When the movable member 25 is moved toward the base 21 by a weight of the user, the top ends of the first projections 22 contact the bottoms of the second grooves 27, and at the same time the top ends of the second projections 26 contact the bottoms of the first grooves 23, without the optical fiber 30 being sandwiched between the top ends of the first projections 22 and the bottoms of the second grooves 27, and between the top ends of the second projections 26 and the bottoms of the first grooves 23. In this case, it is possible to prevent an overload to the optical fiber 30 while providing a required amount of elastic deformation to the optical fiber. In other words, it is possible to prevent a breakage of the optical fiber 30, and improve reliability of the biological-signal detecting device.

Figure 8:
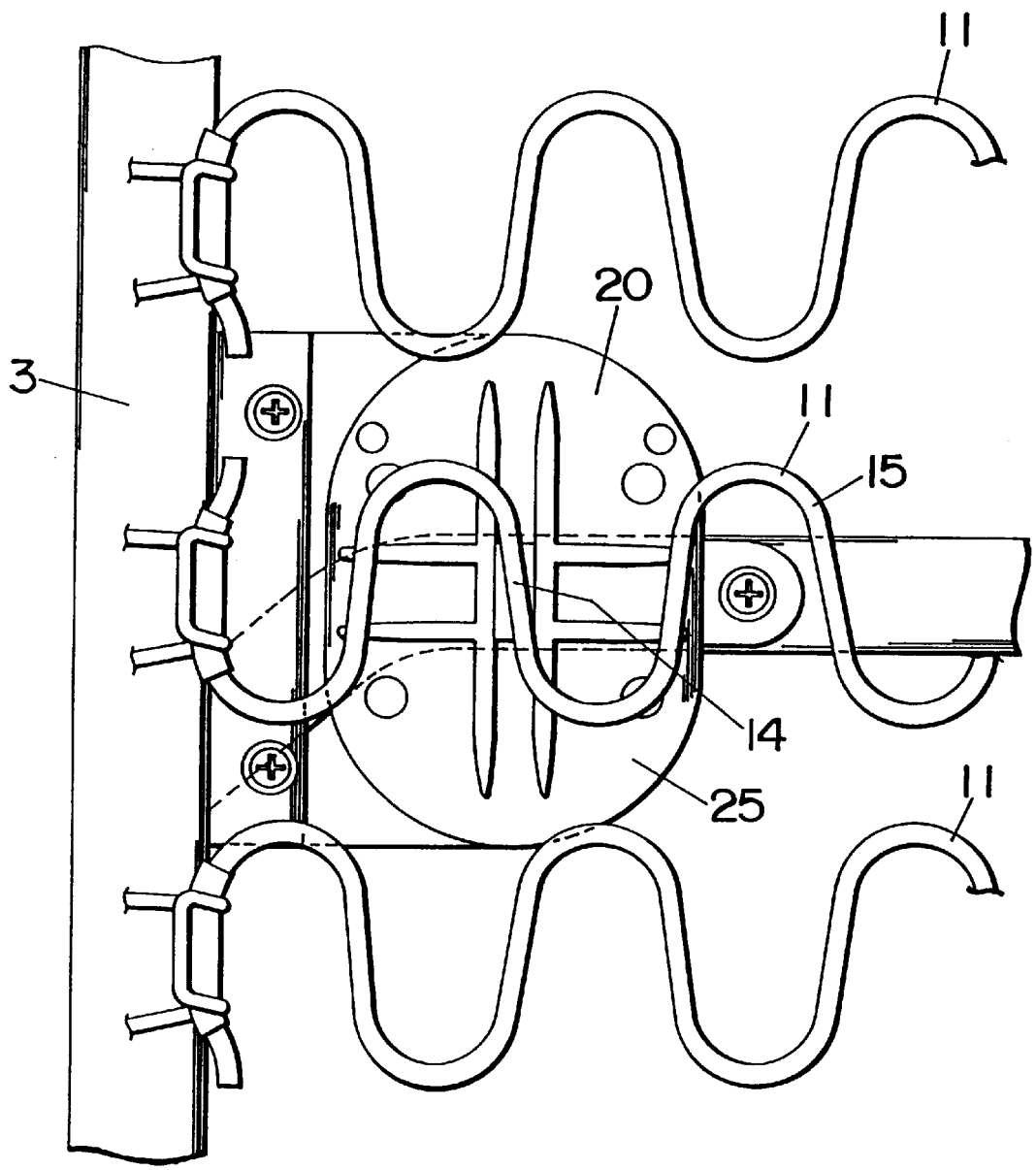
FIG. 8 is a view illustrating the biological-signal detecting unit disposed adjacent to a frame of the chair.

The detecting unit 20, as shown in FIG. 2, can be disposed in the vicinity of a center of the second supporting surface of the spring net 10. When the detecting unit 20 is disposed adjacent to the frame 3 of the chair 1, as shown in FIG. 8, it is possible to further reduce a sense of incongruity caused in the detecting unit immediately after the user sits down the chair 1. Even when the detecting unit 20 is disposed adjacent to the frame 3, the biological vibration of the user can be accurately transmitted to the detecting unit 20 through the spring net 10. Therefore, there is no problem of a degradation of the detection accuracy. In addition, as shown in FIG. 8, when the detecting unit 20 is disposed such that a center portion of the movable member 25 is positioned just under the linear portion 14 of the spring unit 11, it is possible to provide a uniform elastic-deformation of the optical fiber 30 between the base 21 and the movable member 25 when a weight of the user is loaded to the movable member. This is preferable to provide an accurate detection of the biological signal.

A shape of the movable member 25 is not limited to the above. For example, as shown in FIG. 9, it is possible to use a movable member 25A having on its top surface a projecting portion 40A which contacts the second supporting surface of the spring net 10. Alternatively, as shown in FIG. 10, it is possible to use a movable member 25B having an arcuate top surface 40B which contacts the second supporting surface of the spring net 10. These can provide a stable transmission of the biological vibration of the user to the optical fiber 30.

By the way, when a weight of the user is rapidly loaded to the spring net 10 of the chair 1, there is a possibility of deteriorating a life of the optical fiber because of a shock given to the optical fiber 30 through the movable member 25. For improving this problem, as shown in FIG. 11, it is preferred to use a gas spring device 50 having a shock absorbing capability and a vibration damping capability. In this case, even when a weight of the user is rapidly loaded to the spring net 10 of the chair 1, it is possible to elastically deform the spring net at a relatively slow speed without giving such a shock to the optical fiber. In addition, a vibration of the detecting unit 20, which is caused in synchronization with the biological vibration of the user, can be prevented by an inner gas pressure of the gas spring device 50.

Alternatively, a supporting device shown in FIG. 12 can be used. This supporting device comprises a spring member 51A having a shock absorbing capability, and a vibration damping member 52A for preventing a vibration of the detecting unit 20 caused in synchronization with the biological vibration of the user.

Figure 13:
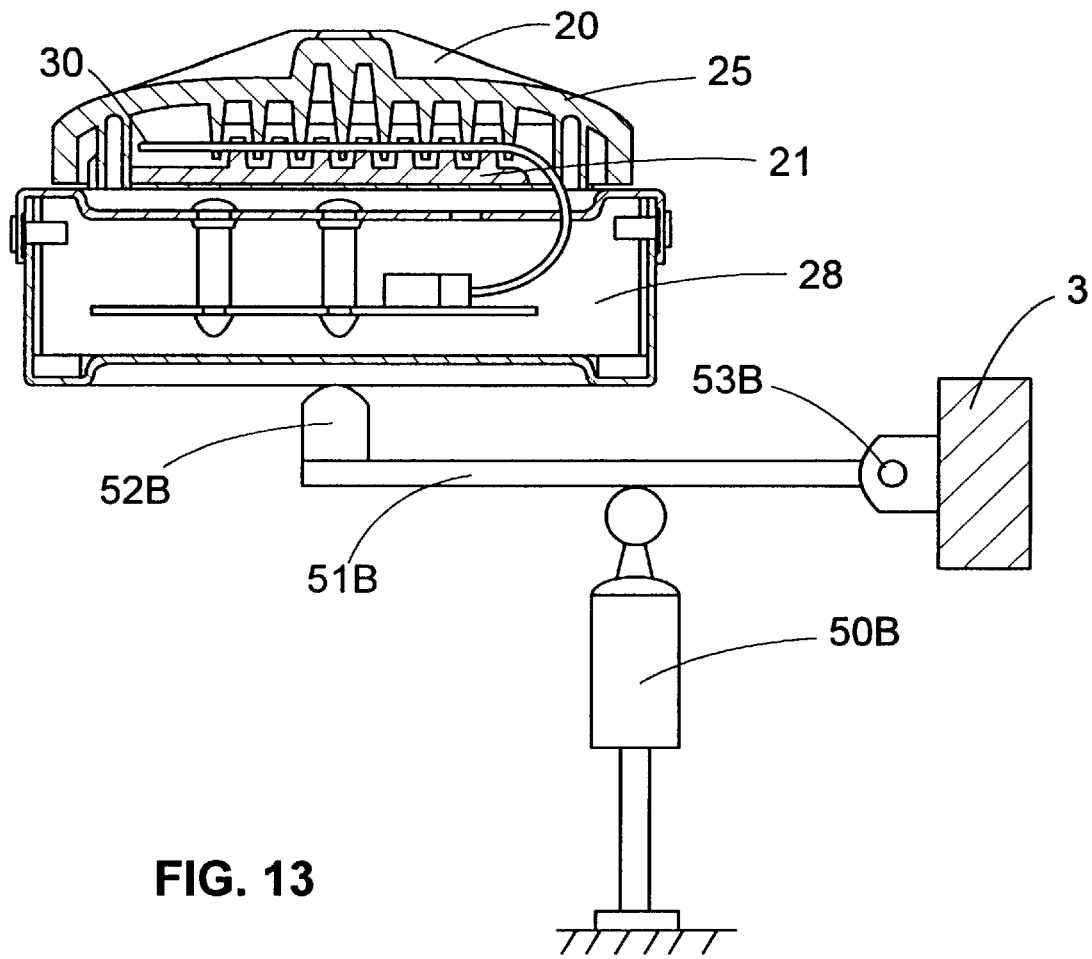
FIG. 13 is a side view of a supporting unit having a link mechanism and a gas spring unit for supporting the biological-signal detecting unit.

In addition, a supporting device shown in FIG. 13 can be used. In this supporting device, the detecting device 20 is coupled with the frame 3 by a connecting rod 51B. A first end 52B of the connecting rod is abutted against a bottom surface of the detecting unit 20, and a second end 53B of the connecting rod is supported to the frame 3 such that the connecting rod can be pivotally moved against the frame about the second end. The connecting rod 51B is also supported at a position between the first and second ends by a gas spring device 50B having a shock absorbing capability and a vibration damping capability. By the use of this connecting rod 51B, it is possible to reduce an amount of displacement of the gas spring device 50B.

Figure 14:
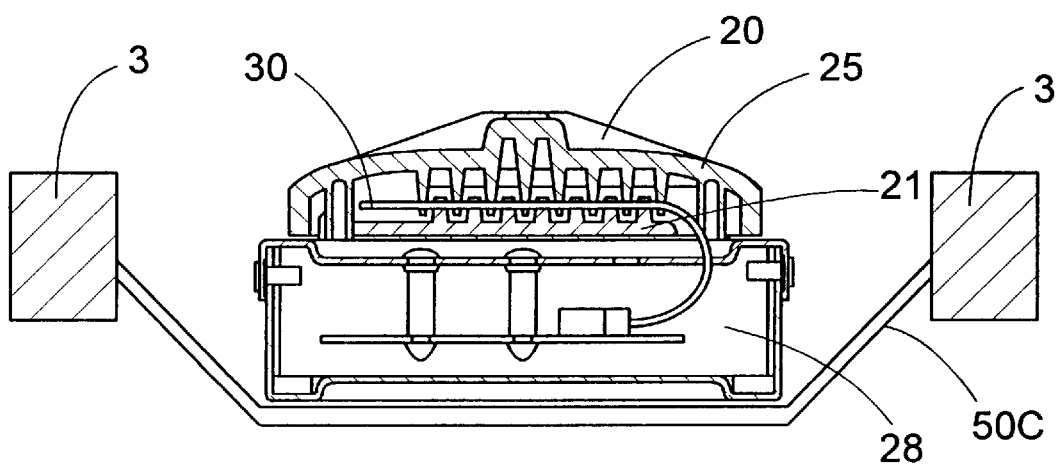
FIG. 14 is a view illustrating a supporting unit for supporting the biological-signal detecting unit.

As shown in FIG. 14, the detecting unit 20 can be supported by the use of a supporting member 50C. This supporting member has a shock absorbing capability and a nonlinear spring characteristic for preventing a vibration of the detecting unit 20 caused in synchronization with the biological vibration of the user. Opposite ends of the supporting member 50C are fixed to the frames 3.

Figure 15:
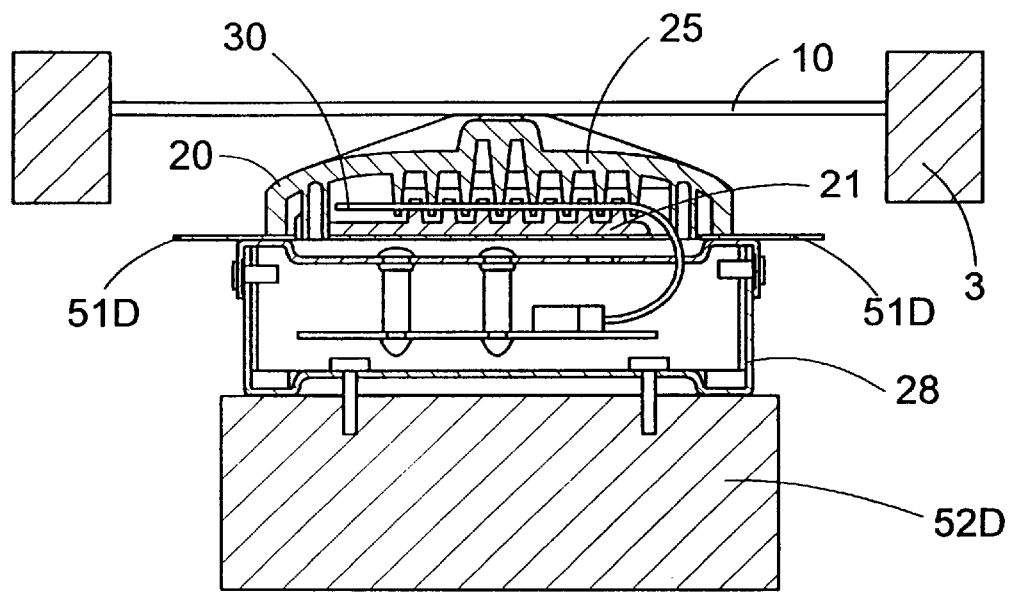
FIG. 15 is a view illustrating another supporting unit for supporting the biological-signal detecting unit.
Figure 16:
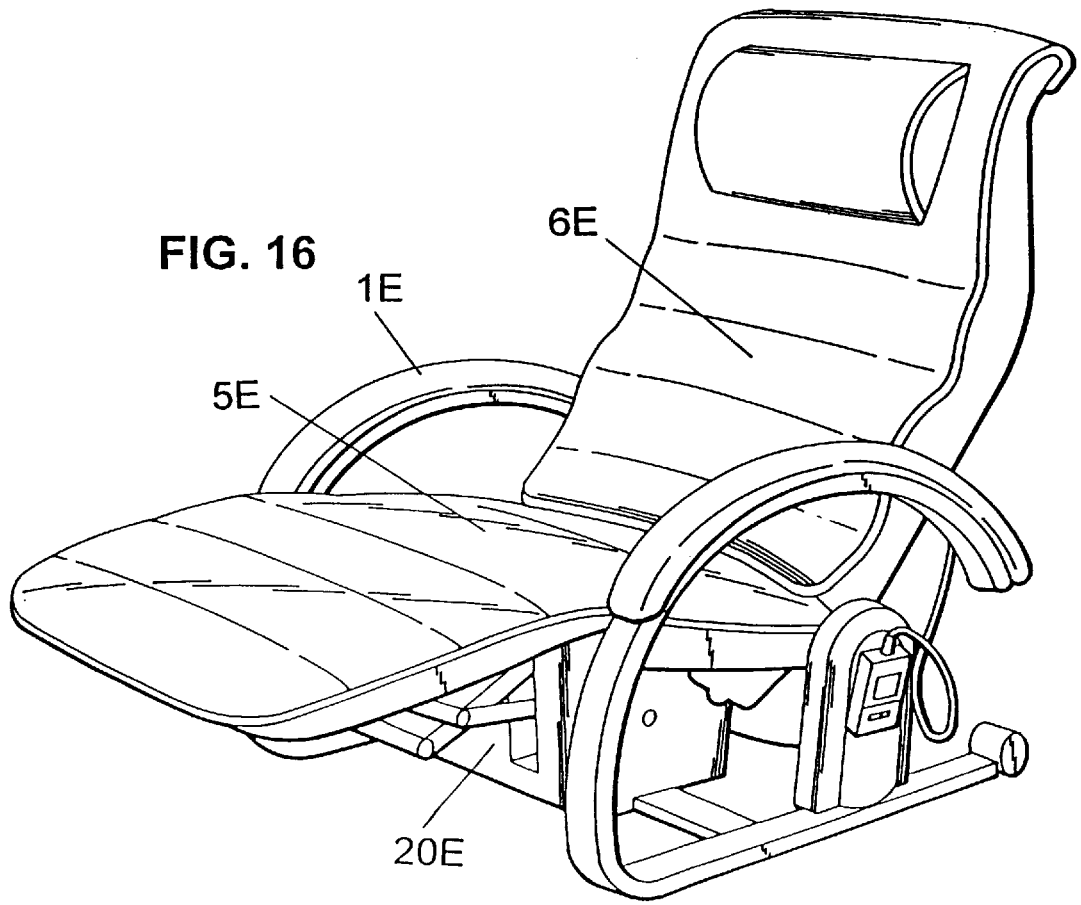
FIG. 16 is a perspective view of a massage chair having a biological signal detecting unit of the present invention.

Alternatively, a supporting unit shown in FIG. 15 can be used. In this supporting unit, an elastic member 51D such as rubber is put between the base 21 and a box 28 incorporating therein a signal detecting circuit. A weight 52D is attached to a bottom of the box 28 to increase a weight of the detecting unit 20. A vibration of the detecting unit 20, which is caused in synchronization with the biological vibration of the user, can be prevented by the use of this supporting unit.

In the above embodiments, the movable member 25 is mounted on the spring net 10. However, the base 21 may be mounted on the spring net 10, if necessary. For example, it is possible to change the arrangement of the detecting unit 20 in FIG. 11 such that the box 28 is mounted on the spring net 10 and the movable member 25 is attached to the gas spring device 50. In this use, the biological vibration of the user is transmitted to the optical fiber 30 through the box 28 and the base 21.

Figure 17:
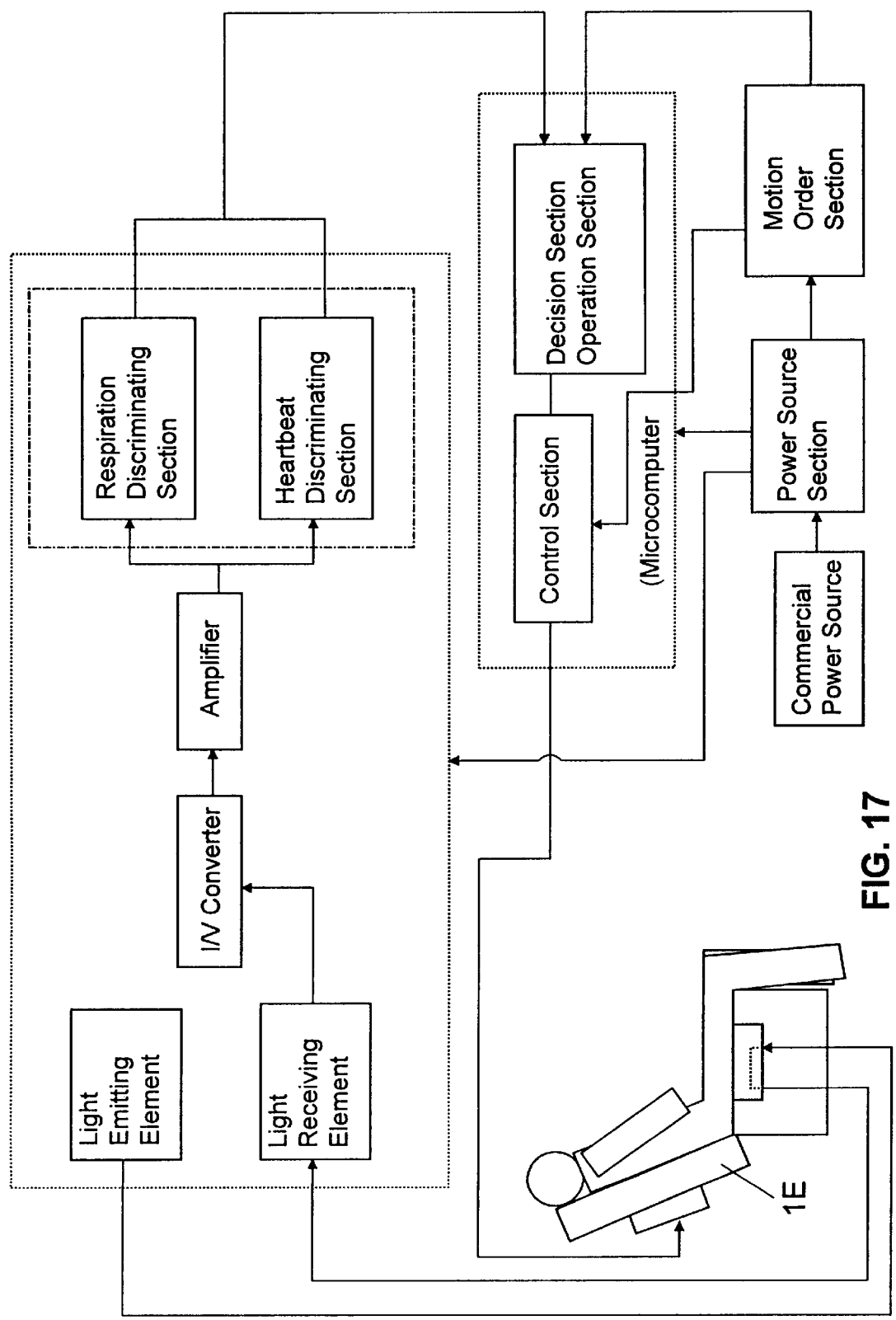
FIG. 17 is an operation control diagram of the massage chair.

As an application of the present invention, a biological-signal detecting device may be used to a massage chair 1E. A biological signal of a user sitting on the massage chair 1E is detected by a biological-signal detecting unit 20E arranged just under a seat portion 5E according to the above-explained manner. According to an output signal of the detecting unit 20E, an optimum amount of massage motion is provided to the user by a massage unit incorporated in a backrest portion 6E of the massage chair 1E. FIG. 17 shows an operation control diagram of the massage chair.

In the above embodiments, the chair having the biological-signal detecting unit is explained as the biological-signal detecting device. However, a bed having the biological-signal detecting unit will provide similar advantages or effects. In addition, it is possible to use a strain gauge or a potentiometer in place of the optical fiber, if necessary.

What is claimed is:

1. A biological-signal detecting device comprising:
   a frame;
   a spring net fixed to said frame and having an elastic deformation capability to support a weight of a user, said spring net having a first supporting surface for receiving said weight and a second supporting surface opposed to said first supporting surface;
   biological-signal detecting means disposed on said second supporting surface, said detecting means detecting a biological signal of the user according to a biological vibration which is a cyclic, minute load-variation of the user transmitted through the spring net when said weight of the user is supported by said spring net.

2. A biological-signal detecting device comprising:

a frame;

a spring net fixed to said frame and having an elastic deformation-capability to support a weight of a user, said spring net having a first supporting surface for receiving said weight and a second supporting surface opposed to said first supporting surface, said spring net comprising a plurality of spring units arranged in a row on a plane, and coupling members for coupling between said spring units, each of said spring units being formed by bending a spring material in a wave pattern, said wave pattern being provided with a plurality of linear portions and arcuate portions each extending between adjacent linear portions; and biological-signal detecting means disposed on said second supporting surface, said detecting means detecting a biological signal of the user according to a biological vibration which is a cyclic, minute load variation of the user transmitted through the spring net when said weight of the user is supported by said spring net.

3. The device as set forth in claim 2, wherein said biological-signal detecting means is disposed on one of said linear portions of said spring nets.

4. The device as set forth in claim 1, wherein said biological-signal detecting means comprises:

a base;

a movable member which is relatively movable to said base according to said biological vibration transmitted through said spring net; an optical fiber having input and output ends, said optical fiber disposed between said base and said movable member so as to show an elastic deformation with a change of internal reflectance according to a position change of said movable member relative to said base;

a light source disposed at said input end to supply a light into said optical fiber;

an optical sensor disposed at said output end to receive an output light from said optical fiber;

analyzing means for analyzing a change of said output light received by said optical sensor, and determining said biological signal, said change of said output light being caused by said change of internal reflectance of said optical fiber when said optical fiber is elastically deformed.

5. The device as set forth in claim 4 comprising supporting means for supporting said biological-signal detecting means, said supporting means having a spring member for preventing that said weight of the user is rapidly loaded to said optical fiber, and a vibration damping member for preventing a vibration of said detecting means caused in synchronization with said biological vibration.

6. A biological-signal detecting device comprising:

a frame;

a spring net fixed to said frame and having an elastic deformation capability to support a weight of a user, said spring net having a first supporting surface for receiving said weight and a second supporting surface opposed to said first supporting surface;

biological-signal detecting means disposed on said second supporting surface, said detecting means detecting a biological signal of the user according to a biological vibration which is a cyclic, minute load variation of the user transmitted through the spring net when said weight of the user is supported by said spring net, said biological-signal detecting means comprising:

a base, a movable member which is relatively movable to said base according to said biological vibration transmitted through said spring net, an optical fiber having input and output ends, said optical fiber disposed between said base and said movable member so as to show an elastic deformation with a change of internal reflectance according to a position change of said movable member relative to said base, a light source disposed at said input end to supply a light into said optical fiber, an optical sensor disposed at said output end to receive an output light from said optical fiber, analyzing means for analyzing a change of said output light received by said optical sensor, and determining said biological signal, said change of said output light being caused by said change of internal reflectance of said optical fiber when said optical fiber is elastically deformed; and gas-spring means for supporting said detecting means, said gas-spring means capable of preventing that said weight of the user is rapidly loaded to said optical fiber, and preventing a vibration of said detecting means caused in synchronization with said biological vibration.

7. The device as set forth in claim 4 comprising supporting means for supporting said detecting means, said supporting means preventing that said weight of the user is rapidly loaded to said optical fiber, and having a nonlinear spring characteristic to prevent a vibration of said detecting means caused in synchronization with said biological vibration.

8. A biological-signal detecting device comprising:

a frame;

a spring net fixed to said frame and having an elastic deformation capability to support a weight of a user, said spring net having a first supporting surface for receiving said weight and a second supporting surface opposed to said first supporting surface;

biological-signal detecting means disposed on said second supporting surface, said detecting means detecting a biological signal of the user according to a biological vibration which is a cyclic, minute load variation of the user transmitted through the spring net when said weight of the user is supported by said spring net, said biological-signal detecting means comprising:

a base, a movable member which is relatively movable to said base according to said biological vibration transmitted through said spring net, an optical fiber having input and output ends, said optical fiber disposed between said base and said movable member so as to show an elastic deformation with a change of internal reflectance according to a position change of said movable member relative to said base, a light source disposed at said input end to supply a light into said optical fiber, an optical sensor disposed at said output end to receive an output light from said optical fiber, analyzing means for analyzing a change of said output light received by said optical sensor, and determining said biological signal, said change of said output light being caused by said change of internal reflectance of said optical fiber when said optical fiber is elastically deformed;

a connecting rod for coupling between said base and said frame, a first end of said connecting rod being pressed against a bottom surface of said base, and a second end of said connecting rod being supported to said frame such that said connecting rod can pivotally move against said frame about said second end; and supporting means for supporting said connecting rod at a position between said first end and said second end, said supporting means capable of preventing that said weight of the user is rapidly loaded to said optical fiber, and preventing a vibration of said detecting means caused in synchronization with said biological vibration.

9. The device as set forth in claim 4, wherein said movable member of said detecting means has a projection through which said biological vibration is transmitted from said spring net to said movable member.

10. The device as set forth in claim 4, wherein said movable member of said detecting means has an arcuate surface through which said biological vibration is transmitted from said spring net to said movable member.

11. A biological-signal detecting device comprising:

a frame;

a spring net fixed to said frame and having an elastic deformation capability to support a weight of a user, said spring net having a first supporting surface for receiving said weight and a second supporting surface opposed to said first supporting surface; and biological-signal detecting means disposed on said second supporting surface, said detecting means detecting a biological signal of the user according to a biological vibration which is a cyclic, minute load variation of the user transmitted through the spring net when said weight of the user is supported by said spring net, said biological-signal detecting means comprising:

a base, a movable member which is relatively movable to said base according to said biological vibration transmitted through said spring net, an optical fiber having input and output ends, said optical fiber disposed between said base and said movable member so as to show an elastic deformation with a change of internal reflectance according to a position change of said movable member relative to said base, a light source disposed at said input end to supply a light into said optical fiber, an optical sensor disposed at said output end to receive an output light from said optical fiber, analyzing means for analyzing a change of said output light received by said optical sensor, and determining said biological signal, said change of said output light being caused by said change of internal reflectance of said optical fiber when said optical fiber is elastically deformed, and a stopper for limiting the relative movement of said movable member to said base such that an amount of elastic deformation of said optical fiber is less than a predetermined value.

* * * * *